United States Patent
Murphy et al.

(10) Patent No.: US 6,593,491 B2
(45) Date of Patent: Jul. 15, 2003

(54) PRODUCTION OF TERTIARY BUTYL ACETATE

(75) Inventors: Carl David Murphy, Sandia, TX (US); R. Jay Warner, Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 09/871,074

(22) Filed: May 31, 2001

(65) Prior Publication Data

US 2002/0010362 A1 Jan. 24, 2002

Related U.S. Application Data

(60) Provisional application No. 60/210,551, filed on Jun. 9, 2000.

(51) Int. Cl.$^7$ ............................................... C07C 69/74

(52) U.S. Cl. ........................................................ 560/240

(58) Field of Search ........................................ 560/240

(56) References Cited

U.S. PATENT DOCUMENTS

| | | | |
|---|---|---|---|
| 3,102,905 A | 9/1963 | Wheeler et al. | 260/497 |
| 3,644,497 A | 2/1972 | Mesich | 260/497 |
| 3,678,099 A | 7/1972 | Kemp | 260/497 |
| 5,866,714 A | 2/1999 | Szady et al. | 560/247 |
| 5,994,578 A | 11/1999 | Karas | 560/247 |

FOREIGN PATENT DOCUMENTS

| | | | |
|---|---|---|---|
| WO | WO 99/54276 | 10/1999 | C07C/67/04 |

*Primary Examiner*—Alan L. Rotman
*Assistant Examiner*—Taylor V. Oh
(74) *Attorney, Agent, or Firm*—M. Susan Spiering

(57) ABSTRACT

Disclosed is a process for the production of t-butyl acetate and coproduction of methyl acetate or ethyl acetate, directly from MTBE or ETBE, by contacting a mixture of acetic acid, acetic anhydride, and MTBE, or alternatively, ETBE, with an acid catalyst. Unlike the art, disclosed is a route employing a tert-butyl ether as starting material for the desired production or coproduction of tert-butyl acetate. Also unlike the art, acetic anhydride is employed to react with the water of formation from the esterification reaction to control formation of t-butyl alcohol.

14 Claims, No Drawings

PRODUCTION OF TERTIARY BUTYL ACETATE

CROSS REFERENCE OF APPLICATION

The present invention was originally filed as provisional application on Jun. 9, 2000 (U.S. Ser. No. 60/210,551).

FIELD OF THE INVENTION

This invention relates to the production of esters and in particular to the production t-butyl acetate.

BACKGROUND

Relevant background information for consideration includes the following, herein incorporated by reference: U.S. Pat. Nos. 3,102,905, 3,644,497, 5,866,714, 5,994,578, PCT WO 99/54276, and U.S. Pat. No. 3,678,099.

The reaction of isobutylene and acetic acid in the presence of an acid catalyst and excess reactant is well known in the art. Tertiary butyl acetate, ("t-BuAc"), is typically produced by an acid catalyzed acetoxylation of isobutylene with acetic acid ("HOAc"). The reaction mixture containing product t-butyl acetate, unreacted acetic acid, and isobutylene, and by-product isobutylene dimer plus any uncreated feed components, is typically fed to distillation columns for recovery of uncreated feed and the purification of the product t-butyl acetate. There are various factors affecting the production of t-butyl acetate, including but not limited to: operating conditions of the fractional column (e.g., temperature, point of feed, rate of feed, rate of withdrawal of product, etc), and, temperature of the reaction mixture as it is fed to the column. A common occurrence is the buildup of (isobutylene) dimer or neutralized catalyst in the column during the distillation process, leading to sludge formation and ultimately requiring shut down and/or clean out of the column.

It is thus desirable to produce t-butyl acetate with an alternative source of acetoxylation target, or in other words, a material more widely available than pure isobutylene. The traditional problems associated with prior art methods are thereby minimized or avoided as well as the high cost of using purified isobutylene.

The present invention provides an advantage in production of t-butyl acetate from readily available and lower cost Methyl Tertiary Butyl Ether ("MTBE"), or Ethyl Tertiary Butyl Ether ("ETBE"), as a raw material, compared to the current use of higher cost isobutylene. The present inventive route also utilizes acetic anhydride production, and optionally, methyl acetate hydrolysis.

SUMMARY

Disclosed herein is a process for the production of t-butyl acetate and co-production of methyl acetate (MeAc), or ethyl acetate (EtAc), directly from MTBE, or ETBE, by contacting a mixture of acetic acid, acetic anhydride, and MTBE, or alternatively ETBE, with an acid catalyst. The catalyst may be a strongly acidic ion-exchange resin, such as a macroreticular type resin.

Typically the reaction pressure is maintained at about 1 to 5 atmospheres and the reaction temperatures are in a range of from about 10° to 100° C., with a preferred temperature range being about 40° to 70° C. However, it will be recognized by those in the art that reaction conditions, including pressures and temperatures, can be varied in accordance with optimal engineering design of the equipment, and operation of the process.

It is preferred to purify the reaction mixture containing t-butyl acetate (t-BuAc), MeAc, or EtAc by fractional distillation or conventional techniques.

BRIEF DESCRIPTION OF THE DRAWINGS

Scheme 1 is a mechanistic scheme of the present invention.

DETAILS OF THE INVENTION

The typical and generally preferred route to t-BuAc is via a purified grade of isobutylene, for example, chemical grade isobutylene. However, the cost and availability of chemical grade isobutylene can be a problem due to the difficulty in separation of isobutylene from other close boiling point hydrocarbons. One method to obtain purified isobutylene is via acid catalyzed cracking of MTBE, followed by a relatively easy separation of the isobutylene from methanol (MeOH) and residual MTBE. This pure isobutylene can then be used in an acetoxylation reactor (see U.S. Pat. No. 3,102,905).

This present invention provides a direct route from commercially available, low cost MTBE to t-BuAc. The reaction is conducted with acid catalysis using acetic acid as a solvent and reactant by addition of acetic anhydride (Ac$_2$O), and MTBE to produce t-BuAc with co-production of MeAc. The MeAc, for example, can be purified for sales, hydrolyzed to methanol and acetic acid for recovery, or used as carbonylation feedstock for production of Ac$_2$O. Also, ETBE, can be substituted for MTBE to co-produce t-BuAc and EtAc.

Scheme 1

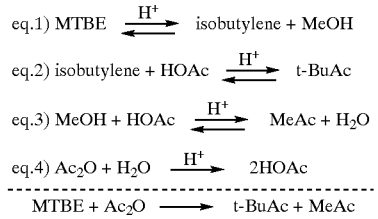

Various competing reactions are occurring in the production of t-BuAc which lead to reaction inefficiency, or lower yield of desired product. Tertiary butyl alcohol (t-BuOH) which can be formed under acetoxylation reaction conditions by the reaction of water with isobutylene, is controlled by the use of Ac$_2$O as a reactant in this invention. The formation of t-BuOH competes with the desired formation of t-BuAc and therefore, represents a raw material efficiency loss. Another reaction inefficiency is via the dimerization of isobutylene primary to form diisobutylene (DIB). The formation of DIB in the reaction step of this inventive process is minimized by utilizing known control techniques that include: lowering the concentration of isobutylene in contact with the acid catalyst, low temperature operation, and by control of the catalyst activity.

The reactions of MTBE and Ac$_2$O in acetic acid are acid catalyzed and can be run in either batch or continuous modes. Reactive distillation can be used to drive the desired reactions to completion by addition of Ac$_2$O/HOAc at the top of the distillation or fractionation column, MTBE feed to the bottom of the column, with MeAc taken as the distillate and a mixture of HOAc and t-BuAc as the residue stream. Pure t-BuAc can be recovered from the reactive distillation column residue by fractional distillation. The reactive distillation overhead MeAc stream could, for example, be purified for sales, used for $Ac_2O$ production by carbonylation, or hydrolyzed to MeOH and HOAc; where the HOAc could be used in production of $Ac_2O$. The preferred reactor for use of MTBE to produce t-BuAc is of plug-flow, fixed catalyst bed design. The heterogeneous acid catalyst can be chosen from a list of typical sources, e.g., zeolites, heteropoly acids, and strongly acidic ion-exchange resins (IER). The preferred heterogeneous catalyst is a macroreticular type strongly acidic ion-exchange resin, for example, Rohm and Haas A-36®. Purification of the crude t-BuAc reaction product involves fractional distillation.

EXAMPLES

The following examples are presented to demonstrate preferred embodiments of the invention. It should be appreciated by those of skill in the art that the techniques disclosed in the examples represent techniques discovered by the inventors to function in the practice of the invention. The experiments run were not optimized. Changes can be made to the specific embodiments which are disclosed and still obtain a like or similar result without departing from the spirit or scope of the invention.

Analyses of the samples obtained during the experimental runs were conducted by gas chromatography. The values in the Tables are the result of reaction conditions, product analyses, and calculations.

Temperatures in the catalyst beds were measured for operation at various reaction conditions and at different catalyst levels. Peak catalyst bed temperatures were generally 10° C. higher than the preheat/coolant settings used in Examples I and II.

The data listed in Tables I and II are for liquid reactor product taken at atmospheric pressure and ambient temperature. The letters A and B represent reactants. Conversion of A=100% (Amount of A in the product)/(Amount of A in the feed) Selectivity of A to B=(Actual amount of B found in the product)/(Amount of B that could have theoretically been made from the amount of A that was converted)×100%.

Example 1
Summarizes the Various Runs Found in Table I.

A mixture containing 47.8 wt. % acetic acid, 28.9 wt. % $Ac_2O$ and 23.9% MTBE was preheated to a temperature of 40° C. and was fed at a rate of 1.85 g/minutes to an ion-exchange catalyst bed containing 6.08 g (8.61 cc) Rohm and Haas A-36® macroreticular ion-exchange resin (Run 13-2). The trickle bed reactor was jacketed and fed coolant at the same temperature as the preheat section, and was operated at atmospheric pressure. The reactor product was analyzed to contain 1.37% isobutylene, 15.24% methyl acetate, 0.52% t-butyl alcohol, 8.61% t-butyl acetate, 59.17% HOAc, 7.24% 2,4,4-trimethyl-1-pentene (dimer), 1.83% 2,4,4-trimethyl-2-pentene (dimer), and 4.33% total trimers and oligomers. The MTBE conversion was calculated to be 98.6% with a selectivity of 27.7% to the tertiary butyl acetate. This same feedstock was fed to the reactor at rates of 3.71 and 7.4 g/minute for Runs 17-2 and 17-4, respectively. The preheat/reactor coolant was lowered to 35° C. and the feed was decreased to 1.86 g/minute for Run 17-6. A mixture containing 47.1 wt. % acetic acid, 27.4 wt. % acetic anhydride, and 25.2 wt. % MTBE was used in Runs 21-2, 21-4, and 21-6, which was approximately 10% (molar) less $Ac_2O$ usage than in other runs.

Data from Example I Runs were Combined in the Following Table I:

TABLE I

A-36 ® IER Catalyzed Acetoxylation of MTBE to t-Butyl Acetate

| Run # | 13-2 | 17-2 | 17-4 | 17-6 | 21-2 | 21-4 | 21-6 |
|---|---|---|---|---|---|---|---|
| Temperature, ° C. | 40 | 40 | 40 | 35 | 35 | 40 | 40 |
| Feed rate, g/min. | 1.85 | 3.71 | 7.40 | 1.86 | 1.86 | 1.86 | 3.66 |
| MTBE Conversion, % | 98.6 | 97.6 | 72.7 | 96.1 | 92.52 | 94.9 | 97.4 |
| Selectivity to t-BuAc, % | 27.6 | 28.9 | 56.3 | 48.2 | 45.4 | 35.7 | 36.2 |
| isobutylene, wt. % | 1.37 | 2.42 | 3.06 | 2.50 | 2.06 | 1.99 | 2.77 |
| methyl acetate, wt. % | 15.24 | 15.34 | 11.72 | 15.23 | 15.34 | 15.73 | 15.07 |
| MTBE, wt. % | 0.33 | 0.55 | 6.47 | 0.90 | 1.87 | 1.27 | 1.83 |
| t-butyl alcohol, wt. % | 0.52 | 0.24 | <0.1 | 0.11 | 0.78 | 1.15 | 0.63 |
| t-butyl acetate, wt. % | 8.61 | 8.82 | 12.81 | 14.49 | 13.93 | 11.23 | 11.68 |
| total dimers wt. % | 9.07 | 8.83 | 1.62 | 5.97 | 6.79 | 8.65 | 7.24 |
| total trimers wt. % | 4.33 | 5.92 | 0.68 | 2.05 | 1.70 | 1.97 | 2.02 |

Rohm and Haas A-36 ® Amberlyst-36 macroreticular ion-exchange resin.
Total oligomer content per run ranged from about 2–15 wt. %, while MTBE conversion ranged from about 72 to 99% conversion.

Example 2
Example 2 Summarizes the Various Runs Found in Table II

A mixture of 23.66 wt. % MTBE, 47.01 wt. % acetic acid, and 28.47 wt. % acetic anhydride was fed to a jacketed, trickle bed reactor containing 6.11 g (10.7 cc) of Rohm and Haas DPT-1® strongly acidic ion-exchange resin. Feed flow rates and preheat/reactor coolant temperatures were varied in a series of runs summarized in the following Table II:

TABLE II

DPT-1 A-36 ® DPT-1 IER Catalyzed Acetoxylation of MTBE to t-Butyl Acetate

| Run # | 33-2 | 33-4 | 33-6 | 37-2 | 37-4 | 37-7 | 37-9 | 41-1 | 41-3 |
|---|---|---|---|---|---|---|---|---|---|
| Temperature, ° C. | 40 | 40 | 40 | 40 | 40 | 40 | 35 | 35 | 35 |
| Feed rate, g/min. | 3.75 | 2.90 | 2.20 | 1.36 | 0.65 | 0.31 | 1.36 | 1.36 | 0.68 |
| MTBE Conversion, % | 69.8 | 72.3 | 75.2 | 87.9 | 93.6 | 96.5 | 75.7 | 78.8 | 88.8 |
| Selectivity to t-BuAc, % | 68.7 | 69.8 | 72.3 | 73.5 | 75.9 | 73.2 | 74.4 | 75.7 | 79.5 |
| isobutylene, wt. % | 2.58 | 2.86 | 2.80 | 2.78 | 2.50 | 2.22 | 2.16 | 2.20 | 2.20 |
| methyl acetate, wt. % | 11.08 | 11.41 | 12.06 | 13.74 | 14.80 | 15.02 | 11.65 | 12.2 | 13.91 |
| MTBE, wt. % | 7.16 | 6.55 | 5.86 | 2.85 | 1.52 | 0.83 | 5.74 | 5.03 | 2.85 |
| t-butyl alcohol, wt. % | 0 | 0 | 0 | 0 | 0 | 0.03 | 0 | 0 | 0 |
| t-butyl acetate, wt. % | 14.95 | 15.75 | 16.96 | 20.14 | 22.13 | 22.02 | 17.58 | 18.60 | 22.57 |
| acetic acid, wt. % | 52.33 | 51.14 | 51.50 | 52.33 | 52.17 | 52.58 | 50.81 | 51.49 | 50.91 |
| acetic anhydride, wt. % | 8.22 | 7.54 | 6.66 | 2.39 | .063 | 0 | 6.79 | 5.52 | 2.89 |
| total dimers, wt. % | 0.29 | 0.25 | 0.27 | 0.63 | 0.94 | 1.53 | 0.56 | 0.21 | 0.30 |

Dimer content from runs in Table II ranged from about 0.2 to 1 wt. %, while MTBE conversion ranged from about 69 to 94% conversion.

The data illustrate the production of t-butyl acetate and methyl acetate from MTBE, acetic acid, and acetic anhydride. The reactants are readily available raw materials. The reaction proceeded with use of a strong acid catalyst. A range of conditions was demonstrated and a range of results was produced. A review of Tables I and II show that the key conversion, i.e., MTBE proceeded with use of a strong acid catalyst. A range of conditions was demonstrated and a range of results was produced. A review of Tables I and II show that the key conversion, i.e., MTBE conversion, ranged from about 69% to about 99%. The key efficiency loss is the dimerization of isobutylene (formed as an intermediate in this process) to oligomers (dimers plus trimers). This inefficiency loss arose due to an irreversible loss of raw material, and it ranged from about 1% to 40%. Although it is desirable to have low amounts of isobutylene and t-butyl alcohol in the reactor product it is envisioned that these two materials can both be recovered by standard techniques and returned to the reactor where they will produce t-butyl acetate using this process.

What is claimed is:

1. A process for production of t-butyl acetate and co-production of methyl acetate directly from MTBE by contacting a mixture of acetic acid, acetic anhydride, and MTBE with an acid catalyst selected from the group of zeolites, heteropolyacids, strongly acidic ionic exchange resins, and macroreticular strongly acidic ion exchange resins.

2. Process for production of t-butyl acetate and co-production of ethyl acetate directly from ETBE (Ethyl Tertiary Butyl Ether) by contacting a mixture of acetic acid, acetic anhydride, and ETBE with an acid catalyst selected from the group of zeolites, heteropolyacids, strongly acidic ionic exchange resins, and macroreticular strongly acidic ion exchange resins.

3. The process of claim 1 wherein conversion of MTBE is greater than about 69%.

4. The process of claim 3 wherein conversion of MTBE is greater than about 75%.

5. The process of claim 2 wherein conversion of ETBE is greater than about 69%.

6. The process of claim 5 wherein conversion of ETBE is greater than about 75%.

7. The process of claim 1 wherein selectivity towards t-BuAc is greater than about 25%.

8. The process of claim 2 wherein selectivity towards t-BuAc is greater than about 25%.

9. The process of claim 1 wherein the reaction pressure is maintained at about 1 to 5 atmospheres and the reaction temperatures are in a range of from about 10° to 100° C.

10. The process of claim 9 wherein the reaction temperatures are in a range of from about 40° to 70° C.

11. The process of claim 2 wherein the reaction pressure is maintained at about 1 to 5 atmospheres and the reaction temperatures are in a range of from about 10° to 100° C.

12. The process of claim 11 wherein the reaction temperatures are in a range of from about 40° to 70° C.

13. The process of claim 1 wherein the acid catalyst is selected from benzene sulfonic acid, toluene sulfonic acid, pyridine sulfonic acid, butane sulfonic acid, cyclohexane sulfonic acid, phosphoric acid, sulfuric acid, heteropolymolybdic acids, heteropolytungstic acids wherein said heteropolymolybdic or heteropolytungstic acids contain central ions which are of phosphorus, arsenic, silicon, germanium, titanium, cobalt, iron, aluminum, chromium, zirconium, gallium, tellurium and boron, sulfonated polystyrene resin, divinylbenzene resin having a pH of about 4.0 to 5.0 meq. H+ per gram of catalyst to between 0.35–2.4 meq.H+ per gram of catalyst, acidic zeolites, beta-zeolites, y-zeoiites, clays, and A-36®.

14. The process of claim 2 wherein the acid catalyst is selected from benzene sulfonic acid, toluene sulfonic acid, pyridine sulfonic acid, butane sulfonic acid, cyclohexane sulfonic acid, phosphoric acid, sulfuric acid, heteropolymolybdic acids, heteropolytungstic acids wherein said heteropolymolybdic or heteropolytungstic acids contain central ions which are of phosphorus, arsenic, silicon, germanium, titanium, cobalt, iron, aluminum, chromium, zirconium, gallium, tellurium and boron, sulfonated polystyrene resin, divinylbenzene resin having a pH of about 4.0 to 5.0 meq. H.+ per gram of catalyst to between 0.35–2.4 meq.H+ per gram of catalyst, acidic zeolites, beta-zeolites, y-zeolites, clays, and A-36®.

* * * * *